United States Patent
Dahmen et al.

(10) Patent No.: US 9,090,828 B2
(45) Date of Patent: Jul. 28, 2015

(54) PROCESS AND DEVICE FOR CONVERTING BIOMASS TO GASEOUS PRODUCTS

(71) Applicant: Karlsruhe Institute of Technology, Karlsruhe (DE)

(72) Inventors: Nicolaus Dahmen, Bruchsal (DE); Andrea Kruse, Bruchsal (DE); Mathias Pagel, Waghaeusel (DE); Hubert Goldacker, Eggenstein-Leopoldshafen (DE); Jens Zimmermann, Merseburg (DE)

(73) Assignee: Karlsruhe Institute of Technology (KIT), Karlsruhe (DE)

( * ) Notice: Subject to any disclaimer, the term of this patent is extended or adjusted under 35 U.S.C. 154(b) by 322 days.

(21) Appl. No.: 13/847,975

(22) Filed: Mar. 20, 2013

(65) Prior Publication Data
US 2013/0213790 A1    Aug. 22, 2013

Related U.S. Application Data

(62) Division of application No. 12/486,261, filed on Jun. 17, 2009, now abandoned.

(30) Foreign Application Priority Data

Jun. 17, 2008 (DE) .......................... 10 2008 028 788

(51) Int. Cl.
*C10B 49/14* (2006.01)
*C10J 3/57* (2006.01)
(Continued)

(52) U.S. Cl.
CPC ................ *C10B 49/14* (2013.01); *B01J 3/008* (2013.01); *B01J 19/30* (2013.01); *B01J 19/32* (2013.01);
(Continued)

(58) Field of Classification Search
CPC ............... C10B 49/14; C10J 3/57; C10J 3/78; C10J 2300/0979; B01J 3/008; B01J 19/30; B01J 19/32; C12P 5/023; Y02E 50/343
USPC ............................ 201/10, 11; 48/197 R, 209
See application file for complete search history.

(56) References Cited

U.S. PATENT DOCUMENTS 3,252,773 A * 5/1966 Solomon et al. ................ 201/10
3,553,279 A    1/1971 Bawa
(Continued)

FOREIGN PATENT DOCUMENTS

DE    202 20 307 U1    4/2003
EP    1 686 192 A1    8/2006

OTHER PUBLICATIONS

N. Boukis et al., "Biomass Gasification in Supercritical Water: First Results of the Pilot Plant," Science in Thermal and Chemical Biomass Conversion, vol. 2, p. 975, 2006.
(Continued)

*Primary Examiner* — Jill Warden
*Assistant Examiner* — Joye L Woodard
(74) *Attorney, Agent, or Firm* — Venable LLP; Robert Kinberg; Tamatane J. Aga

(57) ABSTRACT

A device for converting biomass with a water content of at least 50% to gaseous products includes a reactor filled at least partially with a packing including at least one filler body for accommodating supercritical water and a hydrothermal molten salt. A heater is arranged to heat up the reactor and its content. A first feeding pipe is coupled to the reactor to feed water and salt solution into the reactor. A second feeding pipe is coupled to the reactor to feed to biomass into the reactor. A discharge pipe is coupled to the reactor to discharge gaseous products from the reactor. An outlet is proved in the bottom of the reactor for removing portions of the molten salt.

5 Claims, 1 Drawing Sheet

(51) Int. Cl.
| | |
|---|---|
| *B01J 3/00* | (2006.01) |
| *B01J 19/30* | (2006.01) |
| *B01J 19/32* | (2006.01) |
| *C10J 3/78* | (2006.01) |
| *C12P 5/02* | (2006.01) |

(52) U.S. Cl.
CPC .... *C10J 3/57* (2013.01); *C10J 3/78* (2013.01); *C12P 5/023* (2013.01); *B01J 2219/00123* (2013.01); *B01J 2219/30203* (2013.01); *B01J 2219/30215* (2013.01); *B01J 2219/30265* (2013.01); *B01J 2219/30408* (2013.01); *B01J 2219/30475* (2013.01); *B01J 2219/32466* (2013.01); *B01J 2219/32475* (2013.01); *C10J 2300/0916* (2013.01); *C10J 2300/0923* (2013.01); *C10J 2300/0979* (2013.01); *Y02E 50/343* (2013.01)

(56) References Cited

U.S. PATENT DOCUMENTS

| | | | | |
|---|---|---|---|---|
| 3,708,270 | A | * | 1/1973 | Birk et al. .................. 201/10 |
| 4,113,446 | A | * | 9/1978 | Modell et al. .................. 48/209 |
| 4,500,323 | A | * | 2/1985 | Siegfried et al. ............ 48/197 R |
| 4,822,497 | A | | 4/1989 | Hong et al. |
| 6,878,479 | B2 | | 4/2005 | Cooper et al. |
| 2005/0066573 | A1 | | 3/2005 | Cooper |

OTHER PUBLICATIONS

Y. Raja, "Gasification of Waste to Produce Low-BTU Gass by Molten Salt Technique," J. Institution of Engineers India, vol. 70, Part T2, p. 15, 1989.

G. Lee et al., "Comparison of the Effects of the Addition of NaOH on the Decomposition of 2-Chlorophenol and Phenol in Supercritical Water and Under Supercritical Water Oxidation Conditions," J. Supercritical Fluids, vol. 24, pp. 239-250, 2002.

D.D. MacDonald et al., "Probing the Chemical and Electrochemical Properties of the SCWO System," Electrochimica Acta, vol. 47, pp. 775-790, 2001.

K. Pripopsky et al., "SCWO of Salt Containing Artificial Wastewater Using a Transpiring Wall Reactor: Experimental Results," J. Supercritical Fluids, vol. 40, pp. 246-257, 2007.

M. Hodes et al., "Salt Precipitation and Scale Control in Supercritical Water Oxidation, Part A: Fundamentals and Research," J. Supercritical Fluids, vol. 29, pp. 265-288, 2004.

Z. Sun et al., "Effects of Potassium Alkalis and Sodum Alkalis on the Dechlorination of O-Chlorophenol in Supercritical Water," Chemosphere, vol. 66, pp. 151-157, 2007.

M.D. Bermejo et al., "The Influence of $Na_2SO_4$ on the $CO_2$ Solubility in Water at High Pressure," Fluid Phase Equilibria, vol. 238, pp. 220-228, 2005.

M.D. Bermejo et al., "Bubble Points of the Systems Isopropanol-water, Isopropanol-Water-Sodium Acetate and Isopropanol-water sodium Oleate at High Pressure," Fluid Phase Equilibria, vol. 244, pp. 78-85, 2006.

* cited by examiner

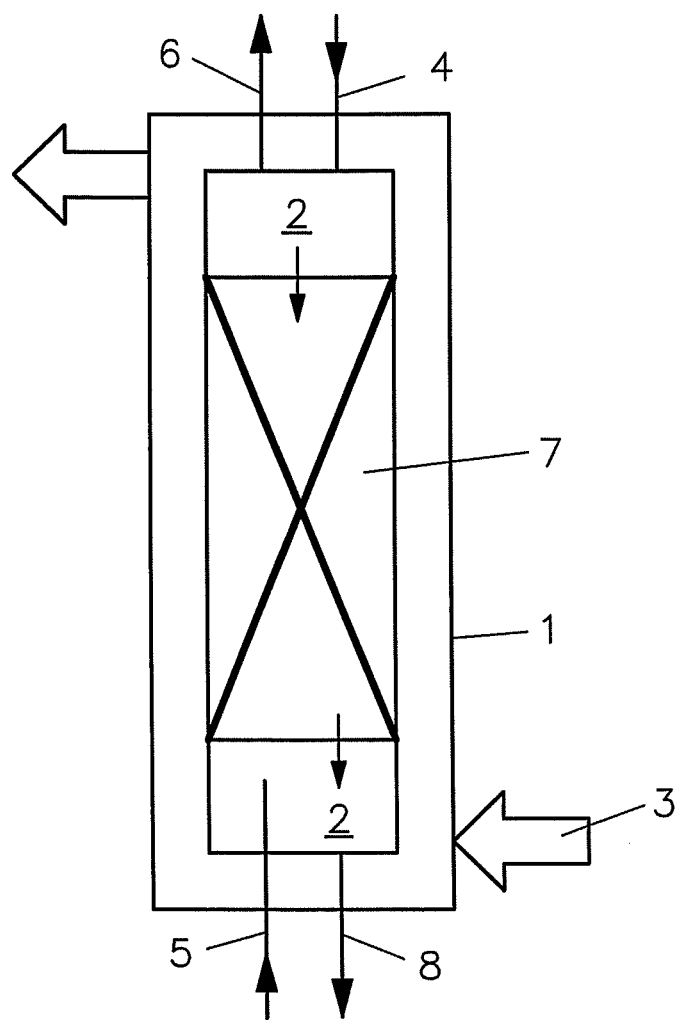

PROCESS AND DEVICE FOR CONVERTING BIOMASS TO GASEOUS PRODUCTS

CROSS-REFERENCE TO RELATED APPLICATION

This application is a divisional application of U.S. application Ser. No. 12/486,261, filed Jun. 17, 2009 which claims the priority of the German Patent Application No.: 10 2008 028 788.1, filed on Jun. 17, 2008, the subject matter of both foregoing applications being incorporated herein by reference.

BACKGROUND OF THE INVENTION

The invention relates to a process and a device for converting wet biomass, meaning biomass having a water content of at least 50%, into gaseous products.

For generating energy from wet biomass through thermolysis or thermal decomposition, supercritical water is often used at temperatures and pressures exceeding the critical point of the water (22.1 MPa and 375° C.). Whereas organic substances are dissolved easily in supercritical water, the inorganic salts precipitate out and can result in clogging up the reactor.

A lean reactor is known from the document by N. Boukis, U. Galla, V. Diem, E. Dinjus, entitled *Biomass gasification in supercritical water: First results of the pilot plant*, published in: A. V. Bridgewater, D. G. B. Boocock, *Science in Thermal and Chemical Biomass Conversion*, cplpress, Volume 2, p. 975, 2006. Salts from the biomass which do not dissolve in the supercritical water collect on the bottom of this lean reactor. Since the precipitated out salts have a sticky to grainy consistency, only the latter can be separated out and only partially through processes such as the sedimentation. The wet biomass until now has been heated to the reaction temperature in an upstream installed heat-exchanger. However, this process is slow and the reaction already starts in the heat exchanger tube, as soon as the necessary temperature is reached.

According to an alternative embodiment, the preheated and concentrated biomass is fed together with the supercritical water into the reactor, which may require in some circumstance an unfavorable ratio between suspended biomass and supercritical heating water. As a result, the heating process is accelerated and the start of the reaction is moved into the reactor, but most of the salts are precipitated out during the operation in an uncontrolled manner and are hard to remove.

U.S. Pat. No. 4,822,497 discloses the use of a pressure vessel as a reactor for the pollutant oxidation in supercritical water. However, the same problems with respect to the salt formation and the precipitating out occur with a pressure vessel as can occur under reactor conditions. To avoid the undesirable and interfering accumulation of salts inside the reactor, the vessel is provided in the bottom region with a water receiver which is kept, with the aid of quenching, at a temperature that is clearly lower than the critical temperature. Under these conditions, the salts from the reaction space above will again dissolve in water. The oxidation in the supercritical water is strongly exothermal and the quenching is therefore energetically acceptable. In contrast, the gasification of a biomass is endothermal and a quenching is energetically not acceptable.

According to Y. Raja, *Gasification of waste to produce low-BTU gas by Molten Salt Technique*, J. Institution of Engineers India, Volume 70, Part T2, page 15, 1989, high conversion rates are achieved during the biomass gasification in dry molten salts, but a large amount of carbon monoxide is also generated in the process. In addition, a shift converter must be installed downstream to generate hydrogen. The forming of charcoal or coke can furthermore not be prevented completely during the conversion with dry molten salts.

German patent document DE 202 20 307 U1 discloses a plant for processing fusible materials in supercritical water. The plant consists of a cylinder-shaped reactor with pressure pipes for supplying the reactant and for discharging the product. The pipe for discharging the product is embodied as stand pipe that projects from above into the reactor chamber and ends in the lower third of the reactor. A bottom outlet is installed on the bottom end of the reactor, which is located at the narrowest point and is provided with a cooler and a valve arrangement for the (dis-)continuous withdrawal from the bottom.

U.S. Pat. No. 6,878,479 B2 discloses a device for the direct conversion of fuels into electrical energy, wherein electrochemical cells containing, respectively, one melted electrolyte are arranged in such a way inside a bipolar, tilted configuration that the electrical resistance between the cells becomes minimal.

A process for the thermal decomposition of graphite fibers and composite polymers in an inert atmosphere is known from the published U.S. Patent Application No. 2005/0066573 A1. With this process, a plurality of graphite fibers bound to a carbonized material are initially produced and the carbonized material is subsequently separated from the graphite fibers with the aid of electro-chemical oxidation in molten salt.

European patent document EP 1 686 192 A1 discloses a process for producing mono saccharides or oligo saccharides from a polysaccharide, wherein the polysaccharide is hydrolized at a pressure of 5 to 100 MPa and a temperature of 140° to 300° C. during a hydro-thermal reaction in hot water, to which carbon dioxide was previously added under pressure.

G. Lee, T. Nunoura, Y. Matsumura and K. Yamamoto disclose in *Comparison of the Effects of the addition of NaOH on the decomposition of 2-chlorophenol and phenol in supercritical water and under supercritical water oxidation conditions*, J. Supercritical Fluids, Volume 24, pp 239-250, 2002, that the influence of NaOH on the decomposition of organic compounds must be taken into consideration when determining the optimum reactor design.

The overview article by D. D. MacDonald and L. B. Kriksunov entitled *Probing the chemical and electrochemical properties of the SCWO system*, Electrochimica Acta, Volume 47, pp 775-790, 2001, describes the advantages and the problems associated with using supercritical oxidation in water (supercritical water oxidation, SCWO). As compared to the combustion process, the SCWO has the advantages of closed cycles when implementing the reaction and higher decomposition efficiency. However, the latter advantage is achieved at the expense of higher corrosiveness.

A reactor configuration is disclosed by K. Pripopsky, B. Wellig and Ph. R. von Rohr in *SCWO of salt containing artificial wastewater using a transpiring wall reactor: Experimental results*, J. Supercritical Fluids, Volume 40, pp 246-257, 2007, available through Science Direct since Jul. 7, 2007. This reactor comprises two different, partially permeable wall elements, which makes it possible to avoid the problem of reactor putrefaction and clogging through salts that precipitate out.

In the document by M. Hodes, P. A. Marrone, G. T. Hong, K. A. Smith and J. W. Tester, entitled *Salt precipitation and scale control in supercritical water oxidation, Part A: Fun-*

*damentals and research*, J. Supercritical Fluids, Volume 29, pp 265-288, 2004, the authors describe the principles of the salt precipitation, the scaling at higher temperatures and pressures, phase diagrams for the salt-water-system, and the resulting phenomena.

The influence of potassium alkalis and sodium alkalis on the de-chlorination of o-chlorophenol in supercritical water is described by Z. Sun, F. Takahashi, Y. Odaka, K. Fukushi, Y. Oshima and K. Yamamoto in *Effects of potassium alkalis and sodium alkalis on the dechlorination of o-chlorophenol in supercritical water*, Chemosphere, Volume 66, pp 151-157, 2007, available online since Jun. 29, 2006.

M. D. Bermejo, A. Martin, L. J. Florusse, C. J. Peters and M. J. Cocero in *The influence of $Na_2SO_4$ on the $CO_2$ solubility in water at high pressure*, Fluid Phase Equilibria, Volume 238, pp 220-228, 2005, describe the effective decomposition of waste material with the example of $Na_2SO_4$ in supercritical water. In the process, decomposition rates of more than 99% were observed for residence times of less than 1 minute.

From M. D. Bermejo, A. Martin, L. J. Florusse, C. J. Peters and M. J. Cocero in *Bubble points of the systems isopropanol-water, isopropanol-water-sodium acetate and isopropanol-water-sodium oleate at high pressure*, Fluid Phase Equilibria, Volume 244, pp 78-85, 2006, it is known that the oxidation in supercritical water represents an effective, high yield technique for the decomposition of organic waste material. As soon as a sufficient number of cations are present, the existing hetero-atoms are precipitated out in the form of salts and can eventually be recovered.

SUMMARY OF THE INVENTION

Based on the above, it is an object of the present invention to provide a device and a process, which do not have the aforementioned disadvantages and restrictions.

In particular, it is an object of the invention to provide a device and process of the foregoing type in which the thermolytic decomposition of the biomass and the forming of additional salts from the biomass take place only inside the reactor, so that the additional salts can be bound directly at the location where they are formed.

It is a further object to provide such a device in which the operation may be continuous.

The above and other objects are achieved according to the invention wherein there is provided, in one aspect of the invention, a device for converting biomass with a water content of at least 50% to gaseous products, comprising: a reactor filled at least partially with a packing material composed of one or several fillers which fill the reactor at least predominantly, completely or partially, for increasing the exchange surface, and for accommodating supercritical water and a hydrothermal molten salt; a heater arranged to heat up the reactor and its content; a first feeding pipe coupled to the reactor to feed water and salt solution into the reactor; a second feeding pipe coupled to the reactor to feed to biomass into the reactor; a discharge pipe coupled to the reactor to discharge gaseous products from the reactor; and an outlet in a bottom of the reactor for removing portions of the molten salt.

According to another aspect of the invention there is provide a process for converting biomass with a water content of at least 50% to gaseous products, comprising:

a) filling a reactor containing a packing comprising at least one filler body with a molten salt comprised of one of a salt or a salt mixture having a melting point below a reaction temperature required for converting the biomass to gaseous products;

b) heating the molten salt so that the molten salt spreads out inside the reactor over the packing with the at least one filler body;

c) feeding a watery biomass into the reactor, wherein the biomass is then heated up to the reaction temperature and comes in contact with the molten salt on the packing with the at least one filler body, thereby resulting in the conversion of the biomass to gaseous products and causing additional salts from the biomass to be bonded to the molten salt;

d) removing portions of the molten salt enriched with additional salts from the biomass from the reactor and replacing of the removed portion of molten salt with a fresh salt solution;

e) removing the gaseous products from the reactor via a discharge pipe; and f) implementing the process above the critical water pressure.

In one embodiment of the invention, the pressure reactor may be an autoclave. In another embodiment the critical water pressure is above 22.5 MPa.

Advantageous filler bodies for the packing should be suitable for an extraction or rectification and should may include ring-shaped, saddle-shaped or grid-shaped filler bodies, structured sheet metal packs, Berl saddles, Braunschweiger Wendeln (packed columns), wire spirals, bubble trays, porcupine packs, machine-wire rings, or mini cascade rings. Filler bodies of this type are available commercially under such trademark titles as Envipac®, Hacketten®, Hel-X®, Hi-flow® rings or saddles, IMTP®, Intalox® saddles, Interpack®, Kühni® structural packs, Leva Ringe®, NOR-PAK®, Montz® structural packs, Novalox® saddles, Pall-Ringe®, RALU-PAK®, Raschig® replacement packs or rings, Snowflakes®, Sulzer® fabric, lamella, or structural packs, Super-Sattel® or Super-Torus-Sattel®, Telleretten®, Top-Paks®, VFF-Net-Balls®, V-Paks® or VSP®.

The material for the filler body must be resistant to the conditions present in the reactor. Suitable materials for this are primarily metals, metal oxides, for example $TiO_2$ or $Al_2O_3$, alloys, such as nickel-based alloys, or carbon.

The process according to the invention is realized in a pressure reactor at a pressure above the critical water pressure, for example above 22.5 MPa. In a first step a), the pressure reactor is filled with a salt solution containing the salt that forms the hydrothermal molten bath, preferably via a first feeding pipe.

The melting point for the salt or the salt mixture used for the molten salt must be below the reaction temperature for converting the biomass to a gaseous product. The reaction temperature as a rule ranges from 550° C. to 700° C.

Advantageously suitable for use are salts that form water-containing melts with low melting points, for example alkali salts such as alkali nitrates, hydroxides, carbonates, phosphates, borates, carbonates or alkali halogenides such as chlorate or perchlorate, ammonium salts and ammonium halogenides, sulfates, carbonates or hydrogen carbonate, or salts of zinc, magnesium, calcium or iron, such as halogenides, and zinc chlorate or perchlorate or iron hydrates.

Examples for suitable salt mixtures are a 50:50 mixture of $NaNO_3$ and $KNO_3$ (melting point 223° C.) or a 56:44 mixture of $LiNO_3$ and $KNO_3$ (melting point 125° C.). Another example for a suitable salt is KOH with a melting point of 360° C.

The salts or salt mixtures used for the molten salt bath furthermore have the following characteristics:
- a sufficient thermal stability for temperatures up to 700° C.;
- the lowest possible corrosiveness;
- the admixture of other salts from the biomass conversion changes the melting point, but only enough so that the process control is not substantially impacted;
- the viscosity ensures the fusibility of the molten salt inside the reactor; and
- the specific heat permits a rapid heating up of the pre-heated biomass through contact with the molten salt.

According to the above described process step b), the molten salt inside the reactor is heated from the outside to the reaction temperature required for converting the biomass to gaseous products, wherein flue gases can be used.

As a result of the increased temperature, the molten salt spreads out over the packing and advantageously flows in downward direction. The molten salt has a noticeably higher density than water under reaction conditions and has a high tendency to creep along walls or inserts, such as the packing.

According to process step c), the watery biomass is then fed into the reactor, for example via a second feeding pipe, causing the biomass to be heated up to the reaction temperature and, in a more or less decomposed form, to come in contact with the hydrothermal molten salt distributed over the packing that consists of the at least one packing body. In the process, the molten salt functions on the one hand as a catalyst for forming the gaseous products, thereby starting the thermolysis of the biomass within a short period of time and providing the biomass carbon in a suitable form for the water separation (the so-called water gas-shift reaction). On the other hand, the molten salt also absorbs the additional salts released during the thermolysis of the biomass.

According to one embodiment, the biomass is initially pre-heated in step c) inside a heat exchanger to a temperature where there is still no interfering decomposition of the organic compounds.

According to process step d), a portion of the molten salt that is enriched with additional salts from the biomass is may be withdrawn continuously via an outlet in the bottom of the reactor, wherein the removed salts are replaced with a fresh salt mixture.

According to process step e), the gaseous products are discharged via a discharge pipe that is preferably arranged on the top of the reactor.

The process according to the invention has the following advantages:
- the thermolytic decomposition of the biomass and thus the forming of the additional salts from the biomass start only at a temperature above the pre-heating temperature and inside the reactor, so that the salts can be bound directly at the location where they are formed;
- the binding of the salts obtained through thermolysis of the biomass takes place in the prepared molten salt bath, which simultaneously functions as heat source for the further heating of the pre-heated biomass to the reaction temperature;
- if the molten salt comprises an alkali salt or a salt mixture where at least one component is an alkali salt, the reactivity of the biomass can additionally be increased during the period of heating up the molten salt from the pre-heating to the reaction temperature, such that the bound carbon atoms contained in the biomass are converted, if possible completely, to $CO_2$ and $CH_4$;
- as a result of the continuous operational control, malfunctions of the system that are caused in particular by pressure fluctuations are avoided;
- owing to the counter-flow principle within the packing, the salts are absorbed efficiently and it is possible to process even biomasses with high salt loads since fresh molten salt comes in contact with a solution depleted of salts and will extract even the last amounts of salt from this solution—the bound salts can thus be removed from the reactor without affecting the operation; and
- the filler bodies in the packing increase the exchange surface between the hydrothermal melt and the biomass-containing solution.

BRIEF DESCRIPTION OF THE DRAWING

The invention is explained in the following in further detail with the aid the single FIG. 1, showing an embodiment of a device according to the invention for realizing the process according to the invention.

DETAILED DESCRIPTION

According to the illustrated embodiment, there is shown a high-pressure reactor (autoclave) 1 that is filled from above via a first feeding pipe 4 with a molten salt 2, intended for producing a hydrothermal molten salt bath that is heated with the aid of a heating 3. The reactor 1 for this example is filled for the most part with a packing 7, consisting of the filler bodies Raschig® rings or Braunschweiger Wendeln (packed columns). A hydrothermal molten salt bath forms as a result of the increased temperature, which has a clearly higher density than water under reaction conditions and therefore spreads out over the packing 7 and flows downward.

A mixture of biomass and water is fed from the bottom into the reactor 1 via a second feeding pipe 5, wherein this mixture is still at the pre-heated temperature that prevents the destruction of the organic compounds in the biomass.

An intensive contact occurs on the filler bodies of the packing 7 between the hydrothermal molten salt bath and the more or less decomposed biomass. In the process, the molten salt functions on the one hand as catalyst for the gasification and, on the other hand, absorbs salts from the biomass.

The gases that form during the continuously occurring process are dissolved in water and are discharged from the reactor 1 via a discharge pipe 6, which in this case is located at the head of the reactor 1. The molten salt 2, which is enriched with the additional salts obtained from the biomass, also flows out continuously through the outlet 8 at the bottom of the reactor 1.

The invention has been described in detail with respect to various embodiments, and it will now be apparent from the foregoing to those skilled in the art, that changes and modifications may be made without departing from the invention in its broader aspects, and the invention, therefore, as defined in the appended claims, is intended to cover all such changes and modifications that fall within the true spirit of the invention.

What is claimed is:

1. A process for converting biomass with a water content of at least 50% to gaseous products, comprising:
   a) filling a reactor containing a packing comprising at least one filler body with a molten salt comprised of one of a salt or a salt mixture having a melting point below a reaction temperature required for converting the biomass to gaseous products;
   b) heating the molten salt so that the molten salt spreads out inside the reactor over the packing with the at least one filler body;

c) feeding a watery biomass into the reactor, wherein the biomass is then heated up to the reaction temperature and comes in contact with the molten salt on the packing with the at least one filler body, thereby resulting in the conversion of the biomass to gaseous products and causing additional salts from the biomass to be bonded to the molten salt;

d) removing portions of the molten salt enriched with additional salts from the biomass from the reactor and replacing of the removed portion of molten salt with a fresh salt solution;

e) removing the gaseous products from the reactor via a discharge pipe; and f) implement the process steps above the critical water pressure.

2. The process according to claim 1, including using an alkali salt for the salt or as a component of the salt mixture.

3. The process according to claim 2, wherein the salt or a component of the salt mixture comprises one of an alkali salt, an ammonium salt or a zinc salt, a magnesium salt, a calcium salt or an iron salt.

4. The process according to claim 3, including using a halogenide for the salt or a component of the salt mixture.

5. The process according to claim 1, including continuously removing portions of the molten salt.

* * * * *